United States Patent [19]

Fraser et al.

[11] 4,430,428
[45] Feb. 7, 1984

[54] COMPOSITION OF MATTER AND PROCESS

[75] Inventors: Thomas H. Fraser, Kalamazoo; Barbara J. Bruce, Portage, both of Mich.

[73] Assignee: The Upjohn Company, Kalamazoo, Mich.

[21] Appl. No.: 327,835

[22] Filed: Dec. 7, 1981

Related U.S. Application Data

[63] Continuation of Ser. No. 119,037, Feb. 5, 1980, abandoned.

[51] Int. Cl.$^3$ ............... C12P 21/00; C12N 15/00; C12N 1/18; C12R 1/865
[52] U.S. Cl. .................................. 435/68; 435/172; 435/942; 435/256; 435/317
[58] Field of Search ............... 435/68, 172, 317, 128, 435/132, 91, 942, 256

[56] References Cited

U.S. PATENT DOCUMENTS 4,237,224 12/1980 Cohen et al. ..................... 435/68

OTHER PUBLICATIONS

Botstein et al., Gene, 8, 17–24, (1979).
McReynolds et al., Gene, 2, 217–231, (1977).
Struhl et al., PNAS, 76(3), 1035–1039, (Mar. 1979).
Beggs, Nature, 275, 104–109, (1978).
Lemke, *Viruses and Plasmids in Fungi*, Marcel Dekker, Inc., New York, 588–589, (1979).
McReynolds et al., Chemical Abstracts, 88:117644w, 258 (1978).
Itakura, K., Hirose, T., Crea, R., Riggs, A. D., Heyneker, H. L., Bolivar, F. and Boyer, H. W., (1977), Science 198: 1056–1063.
Fraser, T. H. and Bruce, Barbara J., Proc. Natl. Acad. Sci., (1978), 75: 5936–5940.

*Primary Examiner*—Esther M. Kepplinger
*Attorney, Agent, or Firm*—Roman Saliwanchik

[57] ABSTRACT

A process for expression of a gene, foreign to the host organism, coding for a protein in a suitable vehicle which comprises taking said gene and fusing it in the correct orientation relative to a transcriptional initiation region present in said vehicle, and inserting said vehicle into a eukaryotic host. Via the subject process, the gene for chicken ovalbumin is expressed in the yeast *Saccharomyces cerevisiae*. Chicken ovalbumin can be used in the food, i.e., baking, industry and also as a protein supplement for animals.

3 Claims, 1 Drawing Figure

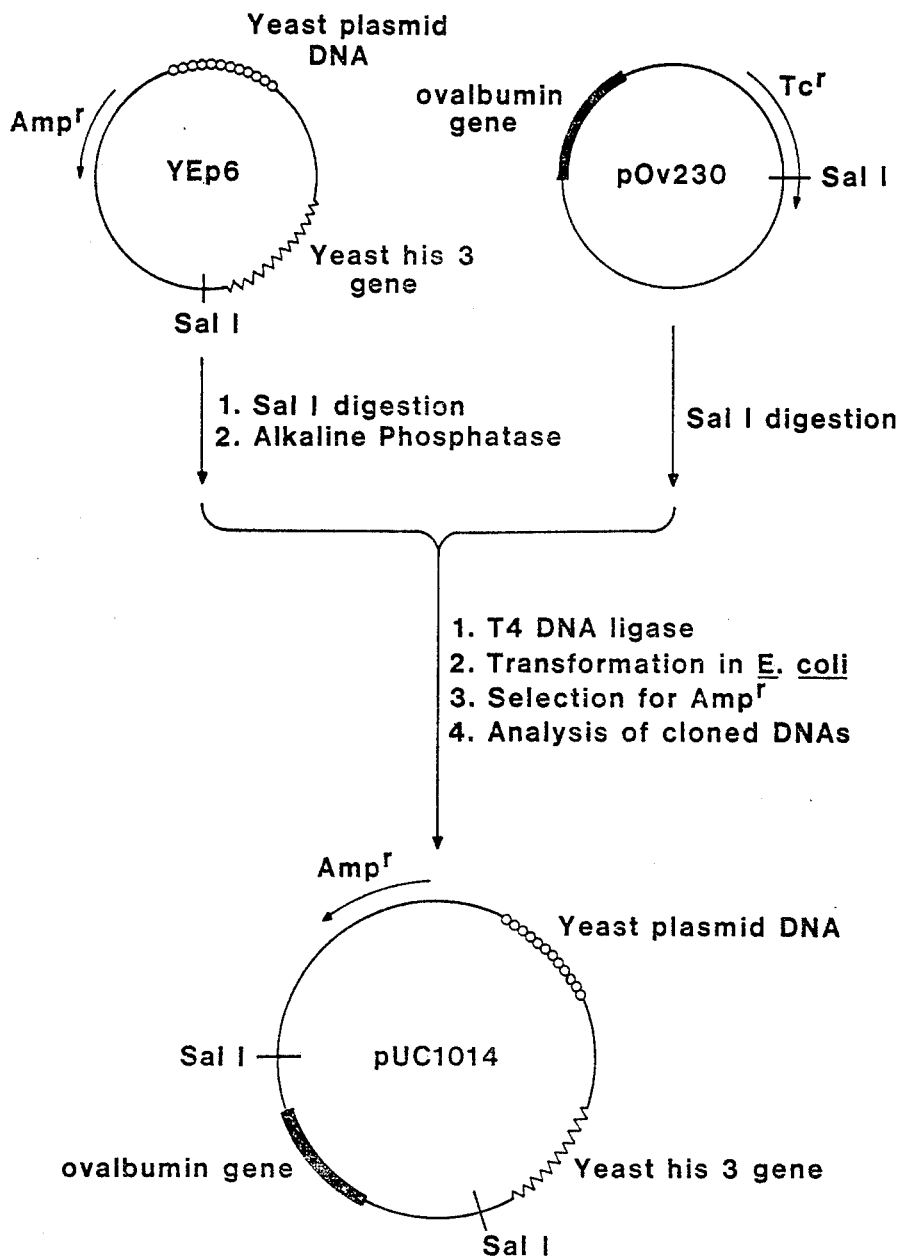

COMPOSITION OF MATTER AND PROCESS

This is a continuation of application Ser. No. 119,037, filed Feb. 5, 1980 now abandoned.

DESCRIPTION

BACKGROUND OF THE INVENTION

Many of the potential benefits envisioned as a result of the application of recombinant DNA technology to medical problems require the insertion into host organisms of genes able to direct the biosynthesis of required proteins. In most cases a protein of interest will normally be synthesized in animal cells and not naturally found in yeasts or other lower eukaryotes. Although it has been possible to clone a number of different animal genes containing the information necessary to code for proteins, reports of the expression of these proteins in bacteria and other unicellular organisms is limited. Some which have been expressed in E. coli are the human polypeptide hormone somatostatin [Itakura, K., Hirose, T., Crea, R., Riggs, A. D., Heyneker, H. L., Bolivar, F. and Boyer, H. W. (1977) Science 198: 1056–1063], rat proinsulin, and human insulin chains.

Previously we succeeded in expressing the chicken ovalbumin gene in E. coli HB101 by fusing said gene near transcriptional and translational initiation regions. See Proceedings of National Academy of Sciences (1978) 75: 5936–5940. In the subject invention, we have succeeded in expressing the chicken ovalbumin gene in yeast by fusing said gene in the correct orientation relative to a transcriptional initiation region.

There is no report in the prior art of any foreign eukaryotic gene being expressed in lower eukaryotes, for example, yeast.

BRIEF SUMMARY OF THE INVENTION

Utilizing recombinant DNA methodology, described infra, the chicken ovalbumin structural gene has been fused to a S. cerevisiae transcriptional control region.

When a plasmid containing the hybrid gene is introduced into S. cerevisiae, a protein identified as ovalbumin by immunoreactivity and polyacrylamide gel electrophoresis is synthesized. The chicken ovalbumin made in yeast is full-length (43,000 MW) and constitutes approximately 1,500 molecules per cell. This is the first animal protein expressed in yeast.

In its broadest aspect, the process of the subject invention is conceived of as a process for expression of a gene, foregin to the host organism, coding for a protein in a suitable vehicle which comprises taking said gene and fusing it near a transcriptional initiation region present in said vehicle, and inserting said vehicle into a lower eukaryotic host.

Examples of other proteins which are within the scope of the subject invention are human serum albumin, human interferons, human antibodies, human insulin, blood clotting factors, brain peptides, enzymes, viral antigens, and proteins from plants.

REFERENCE TO THE DRAWING

The drawing depicts the process steps to make the ovalbumin-fused yeast plasmid pUC 1014. Though the abbreviations used are conventional and well known to those skilled in the art, they are redefined here to facilitate a clear understanding of the invention.

Restriction endonucleases: Sal I (in the Examples).
Tc$^r$—tetracycline resistance gene.
amp$^r$—ampicillin resistance gene.
Yeast his 3 gene—gene coding for an enzyme required for the biosynthesis of histidine in yeast.
T4 DNA ligase—enzyme coded for by bacteriophage T4.
YEp—yeast episomal plasmid.
pUC—official designation for a plasmid owned by The Upjohn Company.
pOV—plasmid ovalbumin.
ovalbumin gene—refers to chicken ovalbumin structural gene.

DETAILED DESCRIPTION OF THE INVENTION

The plasmids YEp 6, pOV 230 and pUC 1014, described herein, have been deposited in E. coli hosts in the permanent collection of the Northern Regional Research Laboratory, U.S. Department of Agriculture, Peoria, Ill., U.S.A. Their accession numbers in this repository are as follows:

HB101—NRRL B-11371
HB101 (pOV 230)—NRRL B-11354
HB101 (YEp 6)—NRRL B-12093
HB101 (pUC 1014)—NRRL B-12094 pUC 1014 has also been deposited in S. cerevisiae SHY 3 strain which is an NIH approved HV 2 host. The accession numbers of these yeast deposits are as follows:

S. cerevisiae SHY 3 strain—NRRL Y-12095
SHY 3 (pUC 1014)—NRRL Y-12096

The above deposits are available to the public upon the grant of a patent. It should be understood that the availability of the deposit does not constitute a license to practice the subject invention in derogation of patent rights granted with the subject instrument by governmental action.

The YEp6 plasmid [Struhl, K., Stinchcomb, D. T., Scherer, S. and Davis, R. W. (1979) Proc. Nat. Acad. Sci. 76: 1035–1039] contains an E. coli replication origin and ampicillin resistance marker derived from pBR322 so that it can be maintained in E. coli. In addition, it contains a yeast plasmid replication origin and yeast His3 gene so that it can be maintained in his$^-$ and yeast auxotrophs. The YEp6 plasmid also has a unique Sal I restriction endonuclease site which can be used for cloning foreign DNA.

Construction of the YEp6-ovalbumin fused plasmid, pUC 1014, proceeds as shown in the drawing. The YEp6 plasmid is cut with Sal I and the resulting linear molecule is treated, advantageously, with alkaline phosphatase to remove the 5' phosphate groups on the ends of the molecule.

The pOV 230 plasmid contains nearly all of the ovalbumin mRNA sequence, including all of the information required to code for the amino acid sequence of chicken ovalbumin [McReynolds, L. A., Catterall, J. F. and O'Malley, B. W. (1977) Gene 2: 217–231]. This plasmid is cut with Sal I, ligated with the alkaline phosphatase-treated, Sal I cut YEp6 and transformed into E. coli. Transformants are selected on ampicillin plates and their plasmid DNA's analyzed.

There are two possible orientations of the ovalbumin gene relative to the YEp6 plasmid, and these can be distinguished by Bam Hl digestion of the DNA and agarose gel electrophoresis.

Preparations of the plasmid DNA's are made by growth in E. coli and used to transform S. cerevisiae. His+ transformants are selected on supplemented minimal media plates under conditions where the His⁻ parents can not grow. The transformants are then grown in broth and lysed by passage through a French pressure cell. The extracts are analyzed for ovalbumin immunoreactivity with an $^{125}$I solid phase radioimmunoassay.

As determined by this immunoassay, only one of the two possible orientations of the ovalbumin gene relative to the YEp6 plasmid is capable of directing the synthesis of ovalbumin in yeast. The hybrid plasmid with this orientation, called pUC1014, requires transcription of the ovalbumin gene in the counterclockwise direction of the plasmid illustrated in the drawing. The other orientation requires transcription in the clockwise direction. Thus, the ovalbumin gene is only expressed in yeast if it is fused into the YEp6 plasmid in the correct orientation relative to a yeast transcriptional initiation region.

Polyacrylamide gel electrophoresis of the chicken ovalbumin made in yeast indicates that it migrates with a mobility almost identical to that of ovalbumin synthesized in chicken oviduct. Some differences in mobility would be expected due to incomplete post-translational modifications of the ovalbumin made in yeast. Thus, the normal translational initiation site of the chicken gene is most probably used by the yeast translational machinery.

The following examples are illustrative of the process and products of the subject invention but are not to be construed as limiting. All percentages are by weight and all solvent mixture proportions are by volume unless otherwise noted.

EXAMPLE 1

DNA Preparation pOV 230 Plasmid DNA from NRRL B-11354 is isolated by the salt precipitation technique described by Guerry et al. [Guerry, P., LeBlanc, D. J. and Falkow, S. (1973) J. Bact. 116: 1064–1066]. L-broth [Lennox, E. S. (1955) Virology 1: 190–206] containing 10 µg/ml tetracycline is inoculated with an overnight broth culture of NRRL B-11354. Cultures are shaken vigorously at 37° C. until the optical density at 600 nm reaches 0.8; plasmid copy number is then amplified for 18 hours with chloramphenicol (250 µg/ml.). Cells are washed once in 50 mM Tris.HCl, pH 8.0, 20 mM EDTA, and resuspended in 33 ml of 25% sucrose in TE (10 mM Tris.HCl, pH 8.0, 0.1 mM EDTA) per liter of culture. Following the addition of 1 mg/ml lysozyme, the suspension is incubated on ice for five minutes, followed by addition of ⅓ volume of 0.25 M EDTA, pH 8.0 and another 5 minute incubation on ice. Cells are lysed by addition of 10% sodium dodecyl sulfate (SDS) in 37 mM Tris.HCl, pH 8.0, 67 mM EDTA, to a final concentration of 1.3% followed by incubation at 37° C. for 30 minutes.

Chromosomal DNA is salted out by bringing the NaCl concentration to 1 M; followed by cooling at 4° C. overnight. SDS and chromosomal DNA are removed by centrifuging at 17,000×g for 30 minutes at 4° C. The resulting supernatant is ethanol precipitated, pelleted, and redissolved in TE. This material is phenol extracted twice, ether extracted, ethanol precipitated, pelleted and resuspended in TE.

Plasmid DNA is further purified by cesium chloride-ethidium bromide density gradient centrifugation. Cesium chloride is dissolved in the DNA solution at a ratio of 1:1 (wt.:vol.), followed by addition of 550 µg/ml ethidium bromide. Gradients are centrifuged for approximately 40 hours at ca. 100,000×g. Plasmid DNA is removed from the gradient by needle puncture, and the ethidium bromide extracted with $H_2O$-saturated 1-butanol. DNA is then dialyzed in 10 mM Tris.HCl, pH 8.0, 0.1 mM EDTA, followed by a final ethanol precipitation. Purified plasmid DNA is dissolved in 10 mM Tris.HCl, pH 8.0, 0.1 mM EDTA.

If ampicillin is substituted for tetracycline in the method described above for preparing pOV 230 DNA, the method can also be used to prepare YEp6 DNA and pUC 1014 DNA in *E. coli*. Other plasmid DNA's can be prepared by this method if an appropriate selection (i.e., another antibiotic) is used to maintain the plasmid in the culture. Also, it is within the skill of those in the art to vary the above conditions to prepare plasmid DNA.

EXAMPLE 2

Restriction Endonuclease Digestions

Sal I digestion of YEp6 DNA and pOV 230 DNA, prepared as described in Example 1, is done in a reaction mixture containing 6 mM Tris.HCl, pH 8.0, 6 mM $MgCl_2$, 150 mM NaCl, 6 mM β-mercaptoethanol, 100 µgm/ml autoclaved gelatin, 80 µgm/ml DNA and 80 units/ml Sal I restriction endonuclease. After incubation for 60 minutes at 37° C., the reaction mixture is phenol extracted, ether extracted and ethanol precipitated. It should be realized that the use of another vehicle might require the use of a different restriction endonuclease.

It is within the skill of those in the art to vary the concentrations of reagents, substrates and enzymes as well as reaction conditions to obtain the desired cleavages.

EXAMPLE 3

Alkaline Phosphatase Treatment

This procedure is carried out essentially as described by Ullrich, et al. [Ullrich, A., Shine, J., Chirgwin, J., Pictet, R., Tischer, E., Rutter, W. J. and Goodman, H. M. (1977) Science 196: 1313–1319] with some minor modifications. Twelve Units/ml of bacterial alkaline phosphatase (BAPF, Worthington) in 20 mM Tris.HCl, pH 8.0, are preincubated at 70° C. for 10 minutes. One hundred µgm/ml of Sal I cut YEp6 DNA, prepared as described in Example 2, is then added and incubation at 70° C. continues for 15 minutes. The reaction mixture is then phenol extracted three times, ether extracted, and ethanol precipitated. This procedure is optional in the preparation of pUC 1014 However, use of the procedure affords a higher ratio of pUC 1014 to parental YEp 6 plasmid among ampicillin resistant transformants, thereby facilitating the recovery of pUC 1014.

EXAMPLE 4

T4 DNA Ligase

In order to ligate the pOV 230 DNA to the alkaline phosphatase treated YEp6 DNA, prepared as described in Example 3, the reaction mixture contains 50 mM Tris.HCl, pH 7.8, 10 mM $MgCl_2$, 20 mM dithiothreitol, 1 mM ATP, 30 µgm/ml YEp 6 DNA, 6 µgm/ml Sal I cut pOV 230 and 15 Units/ml of T4 DNA ligase. After incubation for 16 hours at 12.5° C., the reaction mixture is ethanol precipitated and the pellet dissolved in TCM (10 mM Tris.HCl, pH 8.0, 10 mM $CaCl_2$, 10 mM $MgCl_2$). It is within the skill of those in the art to vary the concentrations of reagents, substrates and enzymes, as well as reaction conditions, to obtain the desired ligations.

EXAMPLE 5

Transformation of E. coli

One hundred twenty ml. of L-broth (1% tryptone, 0.5% yeast extract, 0.5% NaCl) are inoculated with an 18 hour culture of HB101 NRRL B-11371 and grown to an optical density of 0.6 at 600 nm. Cells are washed in cold 10 mM $MgSO_4$ and resuspended for 15 minutes in 20 ml chilled 50 mM $CaCl_2$. Bacteria are then concentrated to one-tenth of this volume in $CaCl_2$ and mixed 2:1 (v:v) with ligated DNA, prepared as described in Example 4. After chilling the cell-DNA mixture for 15 minutes, it is heat shocked at 42° C. for 2 minutes, then allowed to equilibrate at room temperature for ten minutes before addition of L-broth $2\frac{1}{3}$ times the volume of the cell-DNA suspension. Transformed cells are incubated in broth at 37° C. for one hour before inoculating selective media (L-agar plus 20 µg/ml ampicillin) with 200 µl/per plate. Plates are incubated at 37° C. for 48 hours to allow the growth of transformants. Although the transformation procedure is essential for the amplification of biochemically constructed recombinant DNA molecules, the choice of conditions for such a procedure can be changed by those skilled in the art to achieve the desired purpose.

EXAMPLE 6

Transformation of NRRL Y-12095 to NRRL Y-12096

SHY 3 strain of *Saccharomyces cerevisiae* (ura$^-$trp$^-$leu$^-$his$^-$ade$^-$), NRRL Y-12095 is transformed as follows: Twenty ml of log phase culture grown in YEPD broth (1% yeast extract, 2% peptone, 2% glucose) to an $OD_{600}$ of 2.0 ($3 \times 10^7$ cells/ml) were pelleted and resuspended in 1/10 volume 0.9 M sorbitol, 50 mM $KPO_4$ buffer, pH 7.5, 14 mM β-mercaptoethanol. Spheroplasts are formed by addition of 1% Glusulase (Endo Laboratories) and incubation at 30° C. for 60 minutes. After washing three times in 1 M sorbitol, spheroplasts are resuspended in 1/100 original culture volume of 1 M sorbitol, 10 mM Tris-HCl, pH 7.5, 10 mM $CaCl_2$. pUC 1014 DNA is added to a final concentration of 20 µg/ml. After incubation at room temperature for 5 minutes, 10 volumes of 40% polyethylene glycol 4000, 10 mM tris-HCl, pH 7.5, 10 mM $CaCl_2$ are added, followed by 10 minutes incubation at room temperature. His+ transformants are selected by overlaying minimal agar [0.7% yeast nitrogen base (Difco), 2% glucose, 2% agarose, supplemented with 20 µg/ml uracil, adenine and tryptophan and 30 µg/ml leucine] with 0.2 ml cells suspended in 10 ml molten (45° C.) regeneration medium (minimal medium containing 1 M sorbitol, 2% YEPD and 3% agarose). Plates are incubated at 28° C. for 5-6 days.

EXAMPLE 7

Yeast Cell Extract Preparation

Yeast cells grown in 100 ml minimal medium at 28° C. to early stationary phase are washed in Dulbecco's phosphate buffered saline (Gibso) and resuspended in extraction buffer (1 mM Tris-HCl pH 7.4, 1 mM $MgCl_2$, 5 mM NaCl) at a ratio of 1:1 (volume in ml: cell weight in gm). The slurry is put through a French pressure cell twice at 15,000 PSI to lyse the cells.

EXAMPLE 8

Solid Phase Radioimmunoassay

This is done by a slight modification of the method described by Broome and Gilbert [Proc. Nat. Acad. Sci., 75: 2746-2749, 1978]. Polyvinyl chloride sheets (8 mils thick, made by Dora May Co., obtained at Woolworth's) 8 cm in diameter, are floated for 2 minutes at room temperature on 10 ml. of 0.2 M $NaHCO_3$ (pH 9.2) containing 600 µgm of the IgG fraction from anti-ovalbumin goat serum. The polyvinyl is then turned over and the other side coated. The polyvinyl is then washed with a solution (wash buffer) containing phosphate-buffered saline, 0.5% normal rabbit serum and 0.1% bovine serum albumin. After washing, the sheets are placed in contact with protein to be tested for the presence of immunoreactive ovalbumin. If cell lysates are to be tested, it is most convenient to spot the lysate on an agarose gel matrix. Proteins within a polyacrylamide gel matrix can also be tested after they had been separated by electrophoresis. The IgG-coated polyvinyl is placed in contact with either the agarose or polyacrylamide gel matrixes, and incubated in the refrigerator (approximately 4° C.) for several hours. The polyvinyl sheet is then placed in contact with [$^{125}$I] labelled anti-ovalbumin IgG and incubated overnight in the refrigerator. After rinsing in wash buffer, the sheets are autoradiographed with Kodak XR-5 film and a duPont Cronex Hi-plus intensifying screen at −70° C.

EXAMPLE 9

Gene Preparation and Cloning

Structural genes coding for eukaryotic proteins can generally be prepared using their purified messenger RNA's (mRNA's) as starting material. A complementary DNA (cDNA) copy of the mRNA is enzymatically synthesized and then enzymatically made double-stranded. This gene is then joined to a suitable cloning vehicle, usually by the poly dA:poly dT tailing procedure [Jackson, D. A., Symons, R. H. and Berg, P. (1972) Proc. Nat. Acad. Sci. 69: 2904-2909], although this is not always necessary. The vehicle containing the structural gene is then amplified in bacteria. This procedure has been used to prepare the pOV 230 plasmid, as well as plasmids containing globin genes and insulin genes.

EXAMPLE 10

Other Vehicles, Hosts, and Gene Sources

Examples of other vehicles which can be used in the invention are any that can replicate within yeast, such as YEp2, YEp4, YRp7, YEp20. Also vectors that can replicate in other lower eukaryotic hosts.

Examples of other hosts for the vehicle are any *S. cerevisiae* derivative or other fungi. It is recognized that these latter hosts would have to be approved by the NIH Guidelines.

The scope of the invention includes animal proteins, which includes vertebrates, which includes warm-blooded vertebrates, which includes birds, which includes chickens. As noted above, the invention broadly covers proteins that are foreign to the host organism. Within this scope there would then be proteins coded for by genes from plants, and plant and animal viruses.

EXAMPLE 11

Purification of Ovalbumin

The transformed yeast cells of Example 6 are grown in minimal medium [0.7% yeast nitrogen base, 2% glucose, supplemented with 20 mg/ml uracil, adenine and tryptophan, and 30 µg/ml leucine] to early stationary phase, and washed in Dulbecco's phosphate buffered saline (Gibco). The cells, containing ovalbumin, are then resuspended in extraction buffer (1 mM Tris-HCl, pH 7.4, 1 mM $MgCl_2$, 5 mM NaCl) at a ratio of 1:1 (volume in ml: cell weight in gm). The slurry is put through a French pressure cell at 15,000 PSI to lyse the cells. Purification to obtain crystalline ovalbumin, for use in the baking industry or for research purposes, can be done as described [Shepherd, V. and Montgomery, R. (1976) in Methods in Carbohydrate Research, Vol. VII, Whistler, R. L. and BeMiller, J. W. ed., Academic Press, New York, pages 172–174]. Crystalline ovalbumin is listed in the sales catalogues of various fine chemical suppliers.

The work described herein was all done in conformity with physical and biological containment requirements specified in the NIH Guidelines.

We claim:

1. SHY 3 (pUC 1014) having the deposit accession number NRRL Y-12096.
2. Plasmid pUC 1014.
3. A process for preparing chicken ovalbumin which comprises culturing *S. cerevisiae* SHY 3 (pUC 1014), having the deposit accession number NRRL Y-12096, in an aqueous nutrient medium under controlled conditions.

* * * * *